(12) United States Patent
Mikkaichi et al.

(10) Patent No.: US 8,784,438 B2
(45) Date of Patent: Jul. 22, 2014

(54) PERFORATION SUTURING METHOD

(75) Inventors: Takayasu Mikkaichi, Tokyo (JP);
Masayuki Iwasaka, Tokyo (JP);
Kunihide Kaji, Tokyo (JP)

(73) Assignee: Olympus Medical Sysems Corp., Tokyo (JP)

( * ) Notice: Subject to any disclaimer, the term of this patent is extended or adjusted under 35 U.S.C. 154(b) by 0 days.

(21) Appl. No.: 13/305,299

(22) Filed: Nov. 28, 2011

(65) Prior Publication Data
US 2012/0071902 A1 Mar. 22, 2012

Related U.S. Application Data

(62) Division of application No. 11/273,198, filed on Nov. 14, 2005, now abandoned.

(51) Int. Cl.
*A61B 17/04* (2006.01)
(52) U.S. Cl.
USPC ........................................................ 606/144
(58) Field of Classification Search
USPC ................. 606/139, 153, 225, 228, 232, 233, 606/144–147, 213, 215
See application file for complete search history.

(56) References Cited

U.S. PATENT DOCUMENTS

| 5,462,561 | A | 10/1995 | Voda |
| 5,868,762 | A | 2/1999 | Cragg et al. |
| 6,066,146 | A | 5/2000 | Carroll et al. |
| 6,290,674 | B1 | 9/2001 | Roue et al. |
| 6,535,764 | B2 | 3/2003 | Imran et al. |
| 7,875,041 | B2 * | 1/2011 | Mikkaichi et al. ............ 606/144 |
| 2002/0055757 | A1 | 5/2002 | Torre et al. |

FOREIGN PATENT DOCUMENTS

| JP | 2003-299663 A | 10/2003 |
| JP | 2004-000601 A | 1/2004 |

* cited by examiner

*Primary Examiner* — Gregory Anderson
(74) *Attorney, Agent, or Firm* — Scully, Scott, Murphy & Presser, P.C.

(57) ABSTRACT

A perforation suturing method has the steps of: inserting a needle into a wall of a hollow organ at a periphery of the perforation formed in the hollow organ, and piercing the wall; withdrawing the needle from the wall after delivery of an anchor attaching suture thread from the needle, and having the suture thread transit the wall; and tightening the suture thread so that the mated insertion points at the time of insertion of the needle into the wall approximately coincide after having the needle pierce the wall at the periphery of the perforation a plurality of times, and making surfaces of the wall where the insertion points are formed coincide with each other.

4 Claims, 14 Drawing Sheets

PERFORATION SUTURING METHOD

CROSS-REFERENCE TO RELATED APPLICATIONS

This application is a divisional application of U.S. application Ser. No. 11/273,198 filed on Nov. 14, 2005 the entire contents of which are incorporated herein by their reference.

BACKGROUND OF THE INVENTION

1. Field of the Invention

This invention relates to a suturing method using an endoscope. For example, it relates to a method of suturing perforation formed in a wall of a hollow organ.

2. Description of Related Art

When conducting procedures on the interior of the body of a patient, one may cite cases of incisions in the body of the patient by surgical operation, as well as transoral and transrectal endoscopic procedures. As a method of suturing perforations in the abdominal region by surgical operation, there is the method shown in FIG. 6a-6c of U.S. Pat. No. 6,066,146. This suturing method is used when closing incisions in the abdominal cavity. A needle is inserted into the muscular layer of the opening in the abdominal wall, and an anchor attaching suture thread is pushed out from the needle. The suture thread attached to the anchor is tied with the proximal side, and suturing is conducted. Endoscopic procedures are conducted by passing forceps, high-frequency treatment instruments, incision instruments, sutures and the like through the channel of an endoscope. For example, in cases where medical treatment is conducted in the abdominal cavity using an endoscope inserted into a duct or cavity via a natural orifice in the living body such as the mouth, anus or the like, tissue is resected from the abdominal cavity or cut open, forming a perforation, and the medical treatment is conducted by accessing the interior of the abdominal cavity from the interior of the duct or cavity via this perforation. After conducting the medical treatment, the formed perforation is sutured with a suture.

SUMMARY OF THE INVENTION

The perforation suturing method of the present invention includes the steps of: inserting a needle into a wall of a hollow organ at a periphery of the perforation formed in the hollow organ, and piercing the wall; withdrawing the needle from the wall after delivery of an anchor attaching suture thread from the needle, and having the suture thread transit the wall; and tightening the suture thread so that the mated insertion points at the time of insertion of the needle into the wall approximately coincide after having the needle pierce the wall at the periphery of the perforation a plurality of times, and making surfaces of the wall where the insertion points are formed coincide with each other.

BRIEF DESCRIPTION OF THE DRAWINGS

FIG. 8 is a view of the delivery of the anchor after the needle has bored through.

FIG. 19 is a view of the delivery of an anchor after the needle has passed through.

PREFERRED EMBODIMENTS (First Embodiment)

Figure 1:
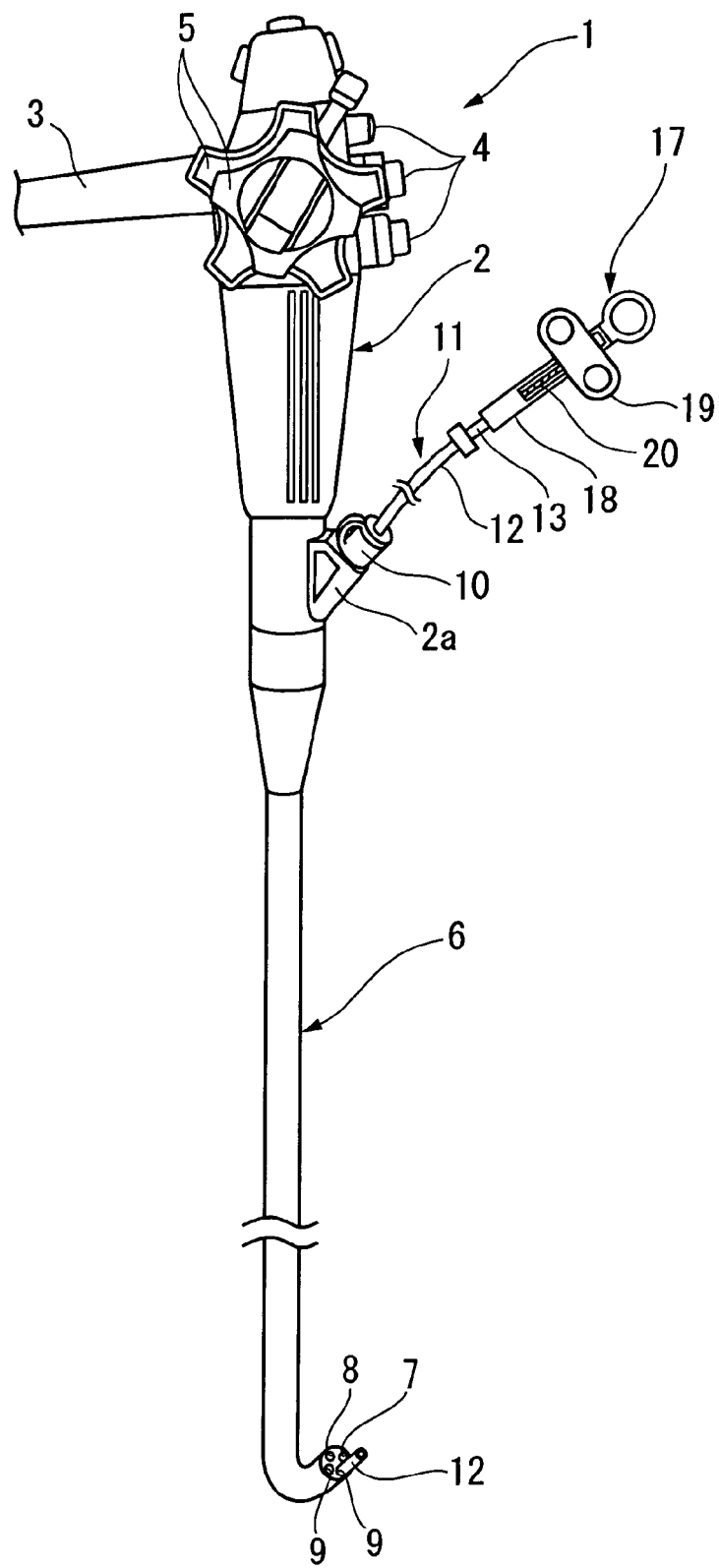
FIG. 1 is a view showing the schematic configuration of an endoscope and a suturing apparatus.

FIG. 1 shows the endoscope and suturing apparatus used in the present embodiment. An endoscope 1 (flexible endoscope) has an endoscope control section 2 that is controlled by the operator. The endoscope control section 2 is connected to a control device by a universal cable 3, and is provided with various types of switches 4 and angle knobs 5. A flexible, elongated endoscope insertion section 6 extends from the distal end of the endoscope control section 2. The distal end of the endoscope insertion section 6 is provided with an observation device 7 for obtaining images of the interior of the body, an illumination device 8, the distal openings of channels 9, and so on. The observation device 7 uses an imaging device provided with a CCD (charge coupled device), optical fiber, and so on. The illumination device 8 has optical fiber that guides the light from a light source. The channels 9 run through the endoscope insertion section 6, and open at a side part 2a of the endoscope control section 2. A cover 10 is attached to the opening of the side part 2a. An insertion aperture is formed in the cover 10, and instruments for medical procedures such as a suturing apparatus 11 are inserted into the channel 9 from this insertion aperture. In short, the endoscope 1 and channel 9 are used as tools for inserting instruments for medical procedures such as the suturing apparatus 11 into a duct or cavity from a natural orifice in the living body.

Figure 2:
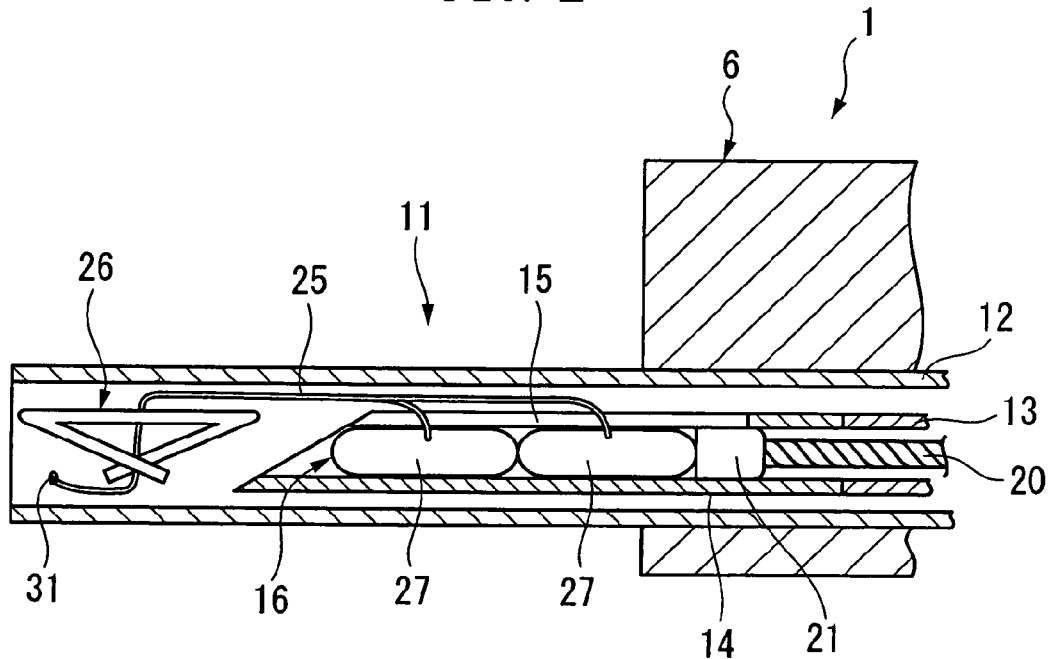
FIG. 2 is a sectional view of the suturing apparatus and the distal end of the endoscope.
Figure 3:
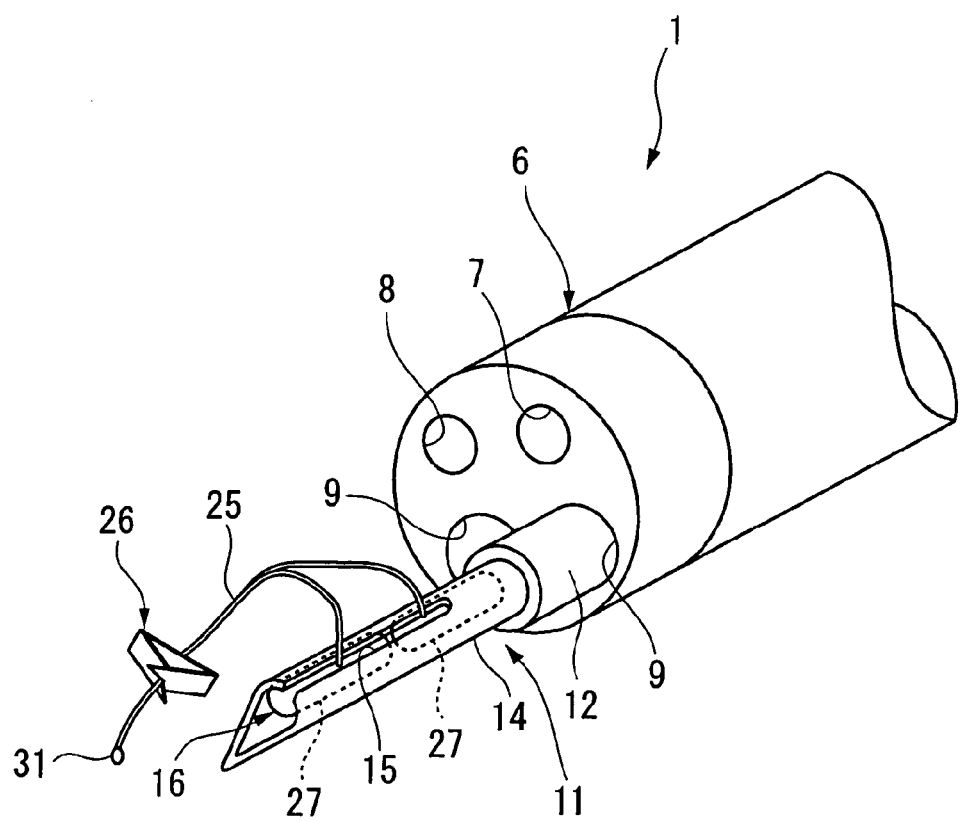
FIG. 3 is an oblique view of the suturing apparatus and the distal end of the endscope.

As shown in FIG. 1 to FIG. 3, a freely movable flexible inner sheath 13 runs through the interior of an outer sheath 12 of the suturing apparatus 11. A needle 14 is fixed to the distal end of the inner sheath 13. A slit 15 extends in the lengthwise direction from the distal end of the needle 14. A suture 16 is housed inside the needle 14. The respective lengths of the outer sheath 12 and the inner sheath 13 are longer than the channel 9 of the endoscope 1. A control section 17 is attached to the base of the inner sheath 13. The control section 17 has a freely slideable handle 19 relative to a control section body 18. The base of a pusher 20 is fixed to the handle 19. The pusher 20 runs through the interior of the inner sheath 13, and extends to the interior of the needle 14. A distal end 21 of the pusher 20 contacts the suture 16.

Figure 4:
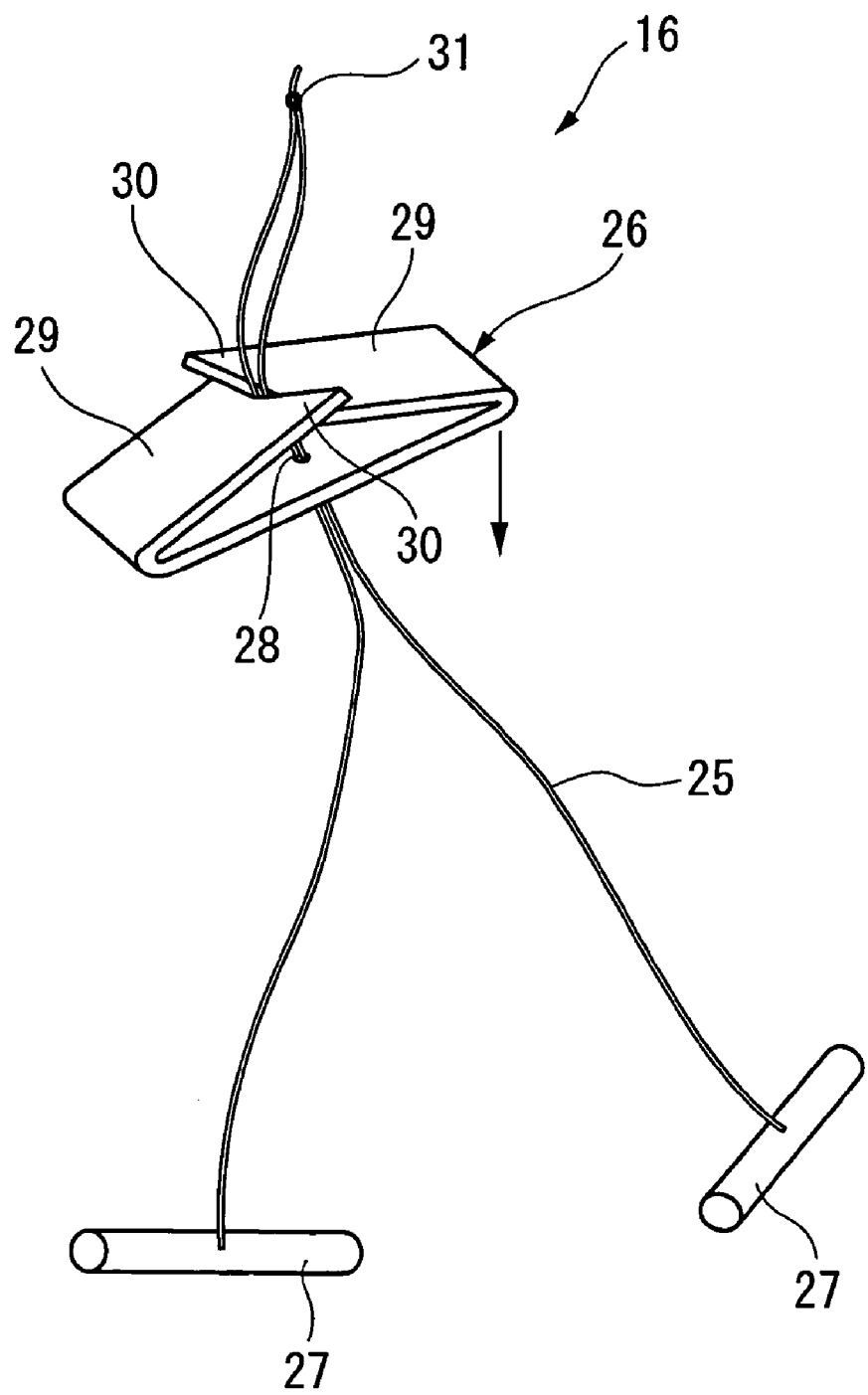
FIG. 4 is a view showing the configuration of the suture.

As shown in FIG. 4, the suture 16 is provided with suture threads 25. The suture threads 25 are largely folded in two, and a knot 31 is formed in the vicinity of the folding point. Furthermore, the suture threads 25 run through a stopper 26 that is approximately triangular in the state where its two ends are bound together. One anchor 27 each is fixed to the respective ends of the suture threads 25. The anchors 27 have a cylindrical shape, and suture thread 25 is affixed to approximately the center of each anchor 27 in the lengthwise direction. The stopper 26 has an aperture 28 at the center in the lengthwise direction of its long plate member through which the suture threads 25 pass. Two ends 29 in the lengthwise direction of the stopper 26 diagonally fold back into each other, sandwiching the suture threads 25. The two ends 29 in the lengthwise direction of the stopper 26 are cut into triangular sections 30. In the stopper 26, the two ends 29 are diagonally folded back so that the sections 30 intersect, and the suture threads 25 are sandwiched in between. Consequently, the suture threads 25 do not fall out from between the ends 29. When the knot 31 of the suture threads 25 is pulled in the direction away from the stopper 26, the two ends 29 of the stopper 26 are slightly opened. Accordingly, the stopper 26 allows movement of the suture threads 25 in this direction. On the other hand, when the ends of the suture threads 25 on the anchor 27 side are pulled, the suture threads 25 move in the direction shown by the arrow mark in FIG. 4. However, at this time, the two ends 29 of the stopper 26 close, and bind the suture threads 25, with the result that the suture threads 25 do not move.

As shown in FIG. 3, two anchors 27 are sequentially housed in the interior aperture of the needle 14 of the suture 16. The suture threads 25 are drawn out from the slit 15 in the needle 14. As shown in FIG. 2, the stopper 26 is housed more toward the distal end than the needle 14 inside the outer sheath 12. The number of anchors 27 and the shape of the stopper 26 are not limited to the illustrated mode.

Next, the suturing method of this embodiment is described primarily with reference to FIG. 5 to FIG. 12. FIG. 5 to FIG. 12 are typical views that serve to explain the technique, and the abdomen (the stomach) is shown as one example of a hollow organ.

Figure 5:
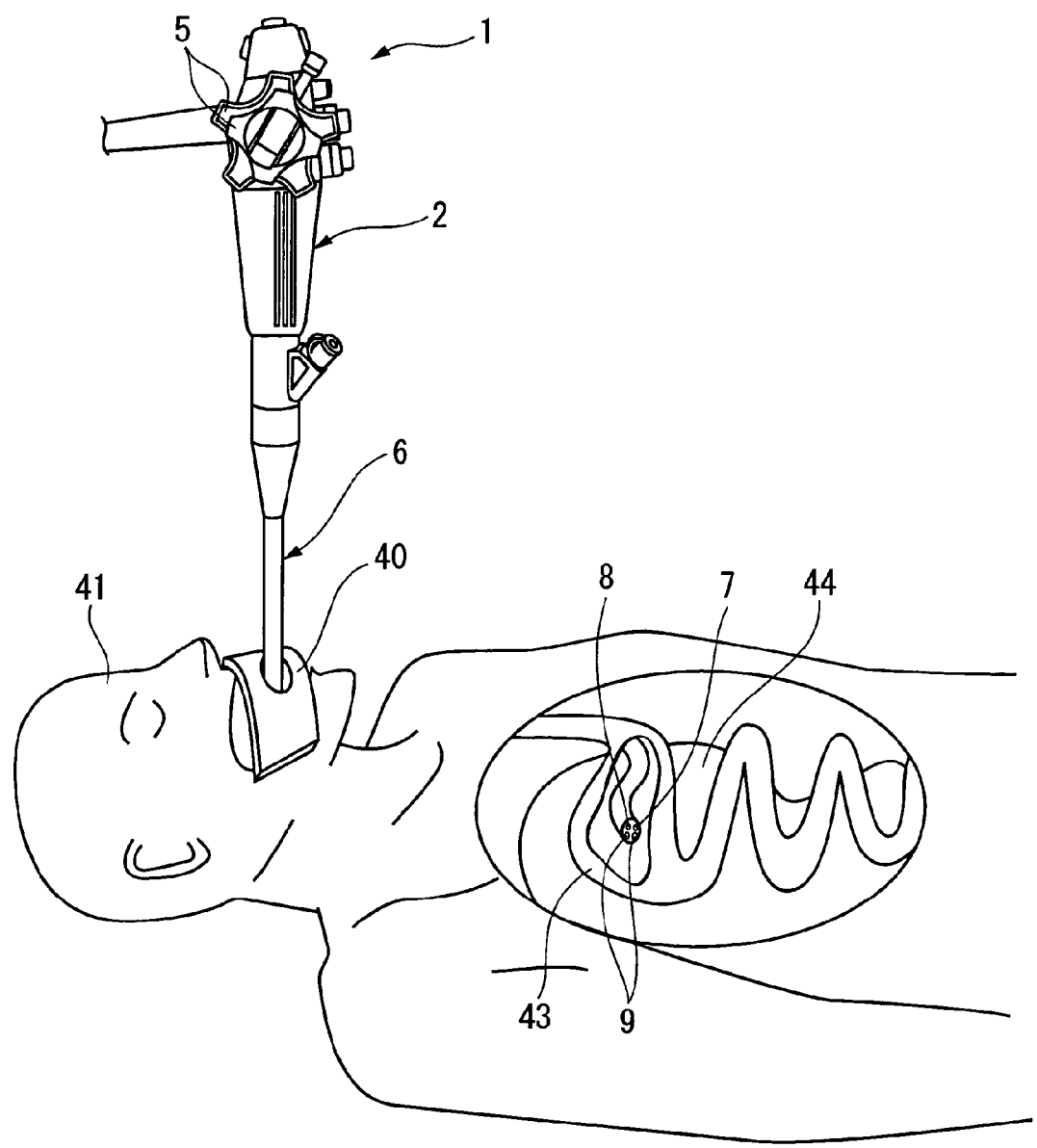
FIG. 5 is a view showing the step of inserting the endoscope into the abdomen of the patient, and observing the planned incision position from inside the abdomen.
Figure 6:
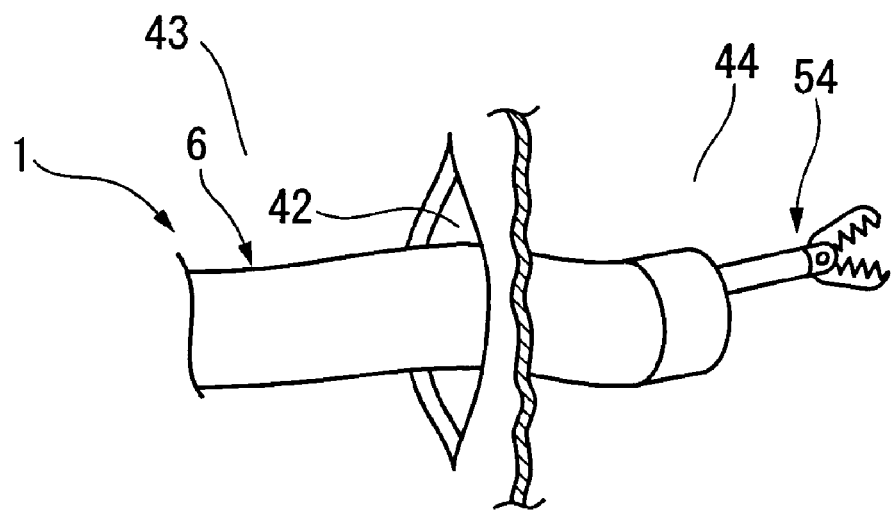
FIG. 6 is a view showing the step of conducting a procedure in the abdominal cavity via a perforation.

As shown in FIG. 5, the endoscope insertion section 6 is inserted from the mouth of a patient to which a mouthpiece 40 is attached, and the distal end of the endoscope insertion section 6 is curved by the angle knob 5. A perforation is formed in a wall of an abdomen 43 by a needle-like knife which is a high-frequency resection instrument in the channel 9 of the endoscope insertion section 6. As shown in FIG. 6, the endoscope insertion section 6 is directed into an abdominal cavity 44 via a perforation 42. Forceps 54 are passed through the channel 9, and the procedure pertaining to an abdominal cavity 44 is conducted with the forceps 54.

Figure 7:
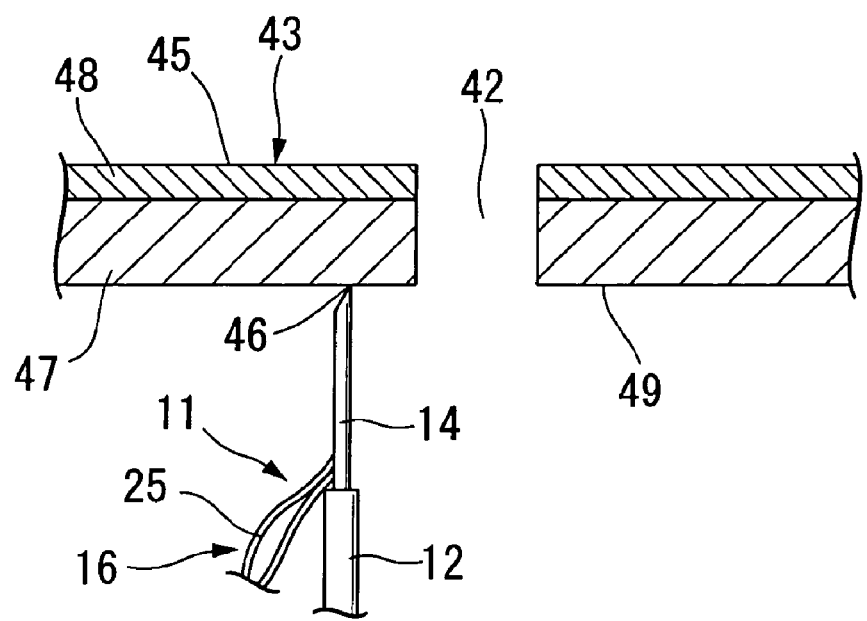
FIG. 7 is a view showing the needle insertion position.
Figure 8:
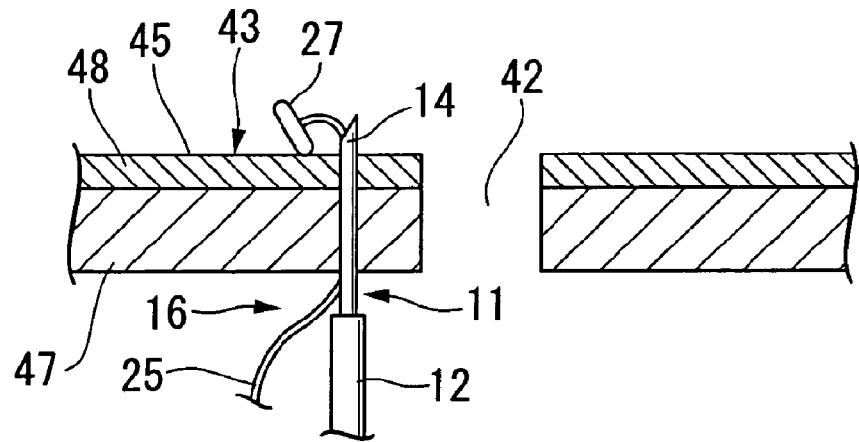

When the procedure is completed, the suturing apparatus 11 is passed through the channel 9 in place of the forceps 54. The distal end of the endoscope insertion section 6 is curved, the distal opening of the channel 9 is oriented toward a wall 45 in the vicinity of the perforation 42 from the outer side (abdominal cavity 44 side) of the abdomen 43, and the needle 14 of the suturing apparatus 11 is projected outward from the outer sheath 12 toward the wall 45. The stopper 26 falls into the abdominal cavity 44 side. As shown in FIG. 7, the needle 14 is inserted at an insertion point 46 at a prescribed distance from the circumferential edge of the perforation 42. When the needle 14 pierces the wall 45 of the abdomen 43 in the sequence of muscular layer 47 and mucous membrane 48, the pusher 20 (see FIG. 2) moves forward. As shown in FIG. 8, first anchor 27 is pushed out from the distal end of the needle 14 to the interior of the abdomen 43. When the needle 14 is withdrawn from the wall 45, the first anchor 27 remains in the interior of the abdomen 43, while the suture thread 25 passes through the wall 45, and is pulled out to the outer side of the abdomen 43.

Figure 9:
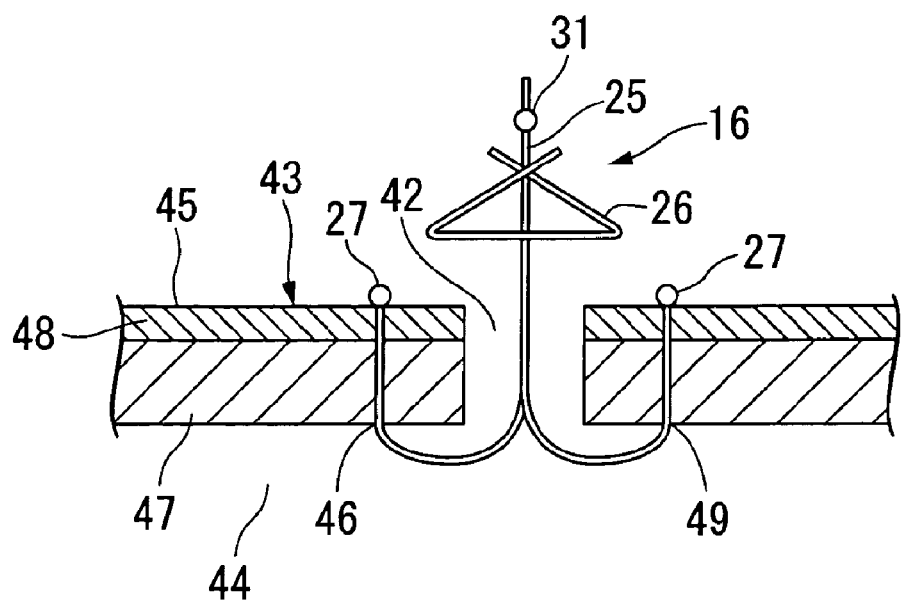
FIG. 9 is a view of the attachment of the suture.

Similarly, as shown in FIG. 7, an insertion point 49 is set at a position that is symmetrical with the insertion point 46 and that sandwiches the perforation 42, and the needle 14 is again inserted at this insertion point 49. When the needle 14 transits the wall 45, a second anchor 27 is pushed out from the needle 14. When the needle 14 is withdrawn, as shown in FIG. 9, the suture 16 is attached in the vicinity of the perforation 42.

Figure 10:
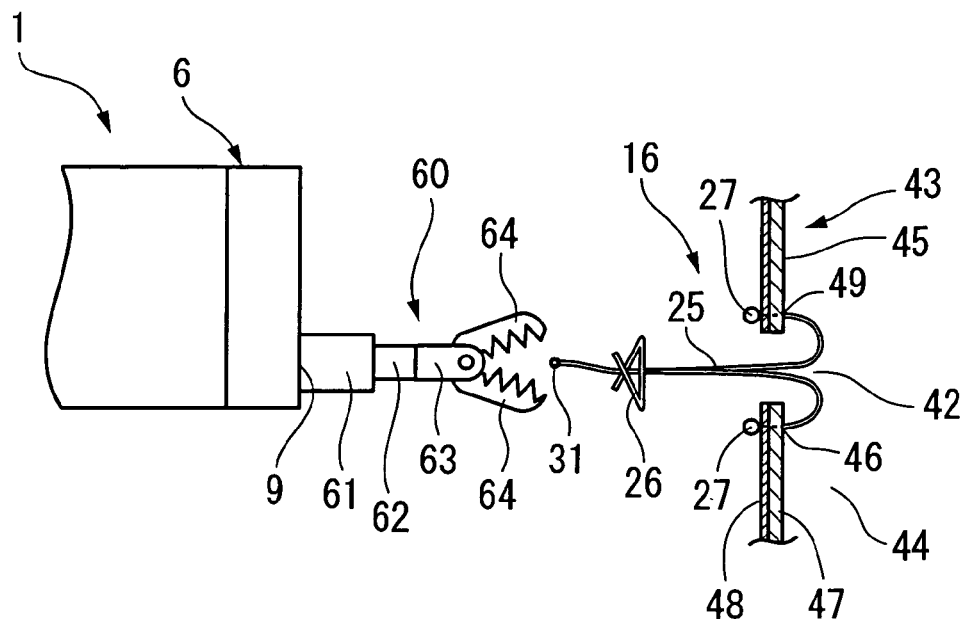
FIG. 10 is a view showing the forceps that tighten the suture.
Figure 11:
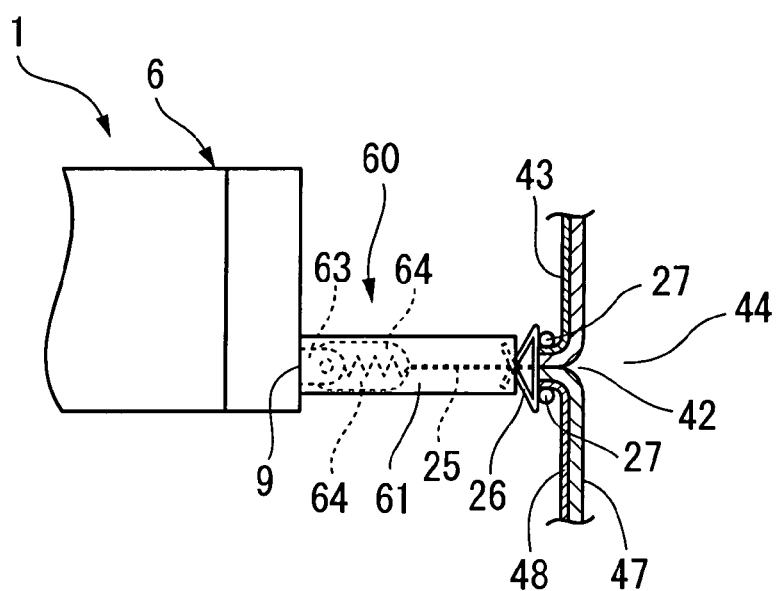
FIG. 11 is a view showing the step of tightening the suture with the outer sheath of the forceps.

Next, as shown in FIG. 10, the endoscope insertion section 6 is brought back to the interior side of the abdomen 43, and the suture 16 is tightened with the forceps 60. With regard to the forceps 60, an inner sheath 62 freely passes backward and forward in an outer sheath 61 which has a larger external diameter than the anchors 27. At the distal end of the inner sheath 62, a pair of clasps 64 are supported by a support member 63 so as to freely open and shut. These clasps 64 clasp the knot 31 of the suture thread 25 of the suture 16. When the outer sheath 61 is moved forward, the distal end of the outer sheath 61 strikes against the stopper 26. A shown in FIG. 11, when the outer sheath 61 is moved further forward, the stopper 26 is pushed inward toward the wall 45. As the stopper 26 is configured to be movable in this direction, the stopper 26 is moved toward the wall 45. As the position of the pair of clasps 64 does not change, the stopper 26 moves forward relative to the suture thread 25. As a result, the distance between the stopper 26 and the anchors 27 diminishes, and the suture thread 25 is tightened.

Figure 12:
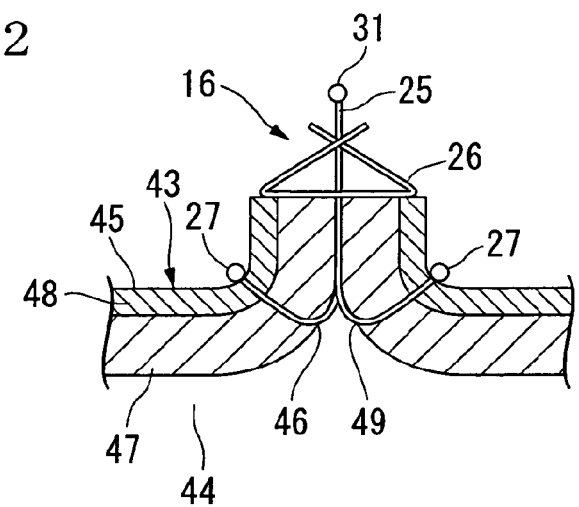
FIG. 12 is a view showing the state where the perforation has been closed to the extent of the tightening of the suture.
Figure 13:
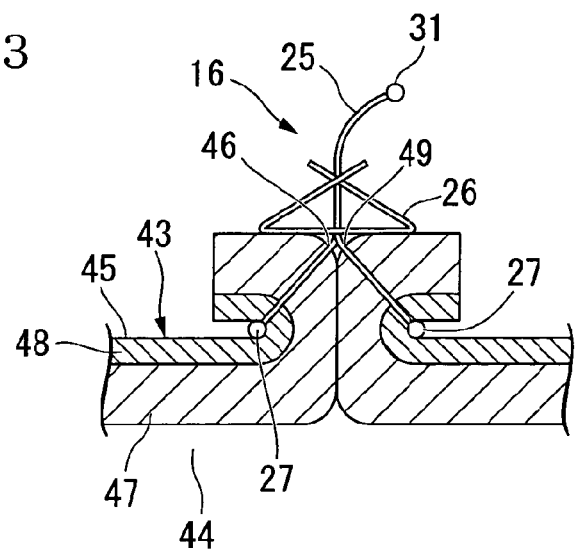
FIG. 13 is a view where the suture has been tightened, and the insertion points have been made to approximately coincide.
Figure 14:
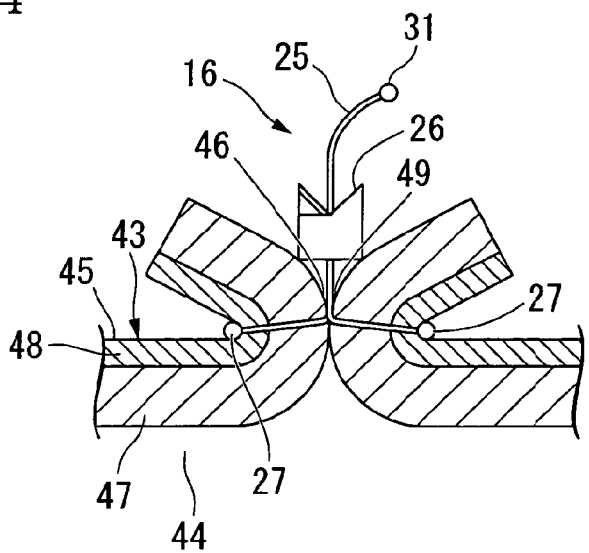
FIG. 14 is a view where the suture has been tightened, and the insertion points have been made to approximately coincide.

As shown in FIG. 12, the process of binding the tissue with the suture thread 25 pulls the tissue between the insertion points 46 and 49 into the interior side of the abdomen 43. Consequently, the muscular layer 47 is sealed with the mated external surfaces (of the abdominal cavity 44 side). The mated insertion points 46 and 49 are brought into proximity so that they approximately coincide on the abdominal cavity 44 side. Finally, as shown in FIG. 13, the tissue between the insertion points 46 and 49 is pulled further into the interior side of the abdomen 43, and the mated insertion points 46 and 49 approximately coincide on the interior side of the abdomen 43. Consequently, the perforation 42 is sutured. The mode for making the insertion points 46 and 49 to coincide is subject to various differences according to the type of the wall 45, the position of the insertion points 46 and 49, and the shape of the stopper 26. FIG. 14 illustrates the case where the stopper 26 is rotated approximately 90° around the suture thread 25, and is vertical. In this state, the stopper 26 is interposed between the tissue that is pulled into the interior side. Even in this case, the mated insertion points 46 and 49 approximately coincide, and the muscular layer 47 is sealed by the mated external surfaces (of the abdominal cavity 44 side).

When suturing of the perforation 42 is completed, the clasps 64 are opened after the outer sheath 61 is withdrawn. The suture thread 25 separates from the clasps 64. The end of the stopper 26 allows movement in the direction of tightening the tissue by the suture thread 25, but works so that the suture thread 25 is tightened in the direction of loosening the suture thread 25. Accordingly, when the suture 16 is stationed inside the abdomen 43, the suture thread 25 maintains the sutured state without loosening.

In this embodiment, the endoscope 1 and the working channel 9 are used as tools through which the needle 14 is passed, the needle 14 inserted via a natural orifice in the living body is inserted into the wall 45 from the abdominal cavity 44 side, and the suture thread 25 is tightened so that these insertion points 46 and 49 are approximately coincided, with the result that it is possible to seal the mated muscular layers. As the mated muscular layers 47 knit together more easily than the mucous membrane 48, the perforation 42 can be rapidly and reliably closed. In the case where the perforation of a hollow organ such as the abdomen 43 is sutured, whereas the knitting of the mated muscular layers takes time with conventional suturing methods, the mated muscular layers 47 knit more reliably, and the perforation 42 is sealed in the present embodiment. As a result, knitting progresses quickly, and healing is quick.

Figure 15:
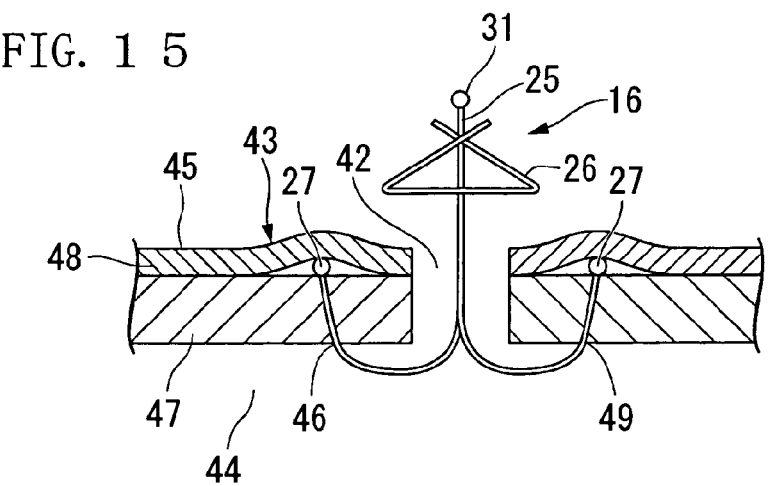
FIG. 15 is a view where the anchors are stationed between the mucous membrane and the muscular layer.
Figure 16:
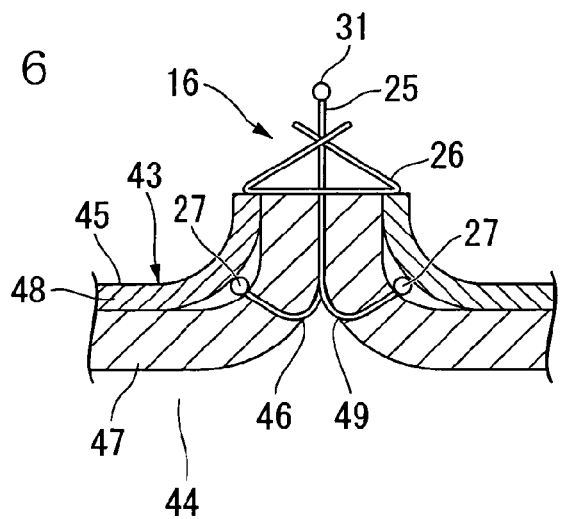
FIG. 16 is a view showing the process of tightening the suture from the state of FIG. 15.
Figure 17:
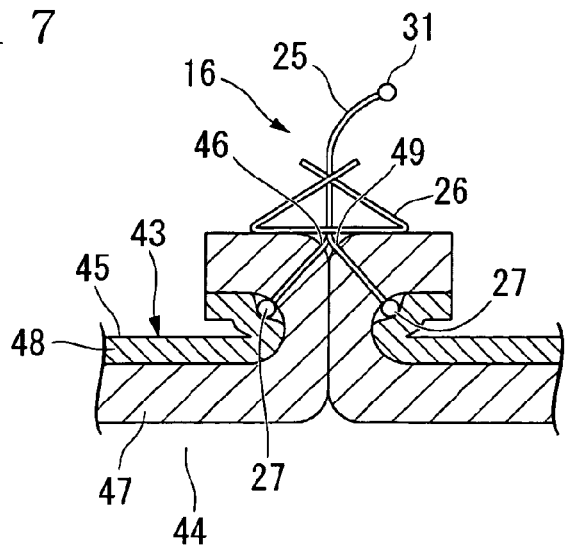
FIG. 17 is a view where the suture is tightened, and insertion points are made to approximately coincide.

As a modified example of this embodiment, there is the suturing method shown in FIG. 15 to FIG. 17. As shown in FIG. 15, the needle 14 pierces the muscular layer 47 from the insertion points 46 and 49, and stations the anchors 27 between the muscular layer 47 and the mucous membrane 48. The suture thread 25 transits only the muscular layer 47, and is attached to the wall 45. As shown in FIG. 16, when the suture thread 25 is tightened, the mated insertion points 46 and 49 are brought into proximity, the tissue is pulled into the interior side of the abdomen 43, and the muscular layer 47 is sealed by the mated external surfaces. As shown in FIG. 17, when the mated insertion points 46 and 49 are made to approximately coincide, the perforation 42 is closed. As the anchors 27 are stationed between the muscular layer 47 and mucous membrane 48, leaks from the interior of the abdomen 43 to the abdominal cavity 44 that pass through the hole formed in the wall 45 due to insertion of the suture thread 25 are prevented. Moreover, as the anchors 27 are not exposed on the interior side of the abdomen 43, the anchors 27 are protected from gastric juices. Furthermore, as the anchors 27 are not exposed to the interior side of the abdomen 43, the anchors 27 can be preserved in an almost sterile state. In this case, healing is promoted.

(Second Embodiment)

A second embodiment of this invention is described with reference to drawings. Description of components and operations identical to those of the first embodiment is omitted.

Figure 18:
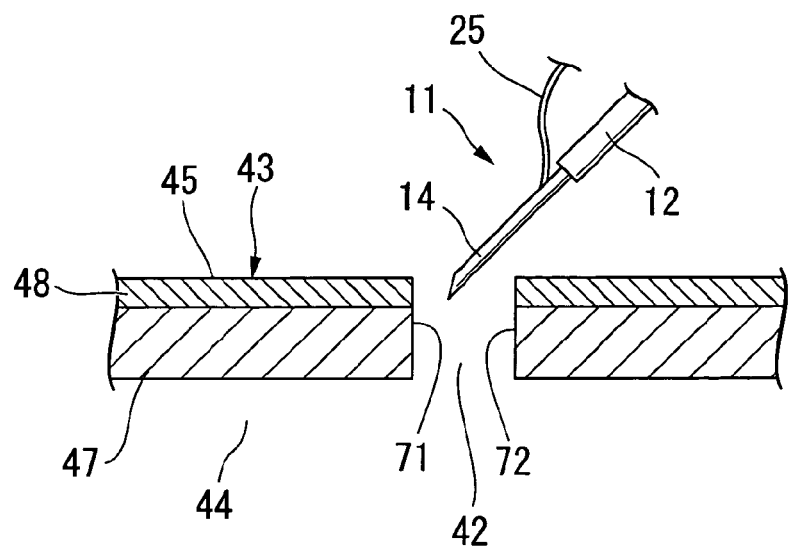
FIG. 18 is a view showing the step of diagonal insertion of the needle into the inner circumferential surface of the perforation.
Figure 19:
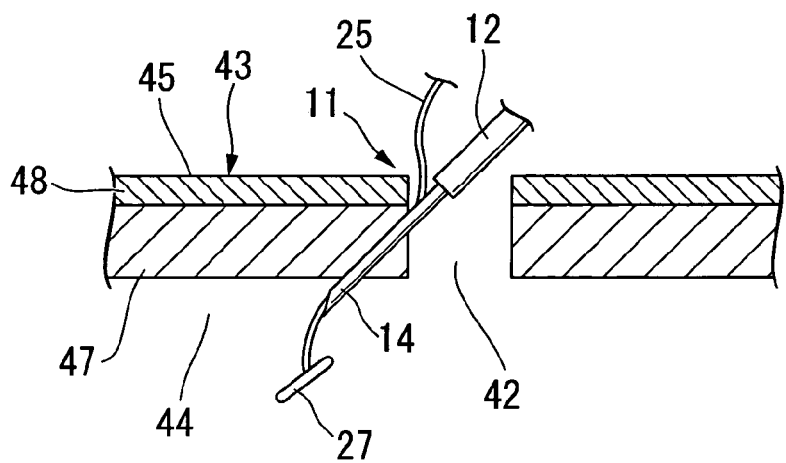
Figure 20:
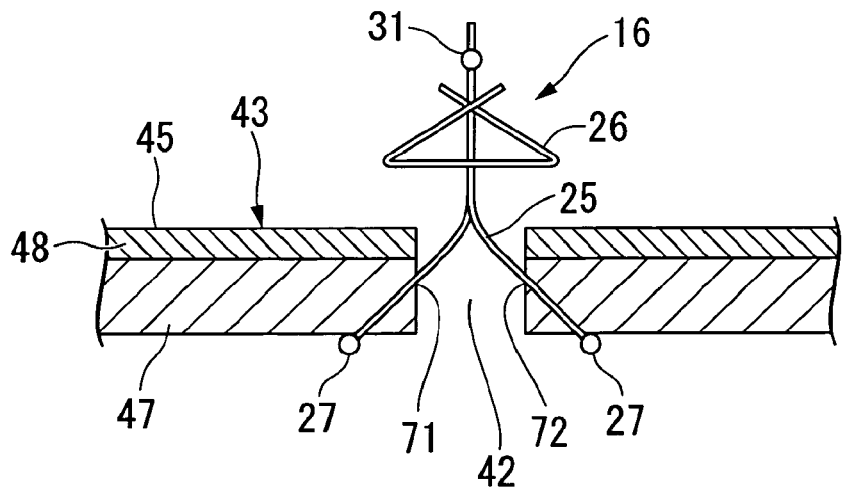
FIG. 20 is a view of the attachment of the suture.

As shown in FIG. 18, the suturing apparatus 11 is passed through the channel of the endoscope insertion section 6. The needle 14 is diagonally inserted at the prescribed insertion point 71 of the muscular layer 47 that is exposed on the inner circumferential surface of the perforation 42. As shown in FIG. 19, when the needle 14 inserted from the insertion point 71 diagonally pierces the muscular layer, and when the distal end of the needle 14 is exposed on the abdominal cavity 44 side, first anchor 27 is pushed out onto the abdominal cavity 44 side. The needle 14 is withdrawn, and is then diagonally inserted at the prescribed insertion point 72 of the muscular layer 47 that is exposed on the inner circumferential of the opposite side of the perforation 42 as shown in FIG. 18. It is preferable that insertion point 71 and insertion point 72 be at approximately identical positions in the thickness direction of the wall 45. When the needle 14 diagonally pierces the abdominal cavity 44 side from the inner circumferential side of the perforation 42, the second anchor 27 is pushed out onto the abdominal cavity 44 side. When the needle 14 is subsequently withdrawn from the wall 45, as shown in FIG. 20, the second anchor 27 is stationed on the abdominal cavity 44 side in the same way as the first anchor 27. After the suture thread 25 has diagonally pierced the muscular layer 47, it transits the interior side of the perforation 42, and is drawn into the abdomen 43.

Figure 21:
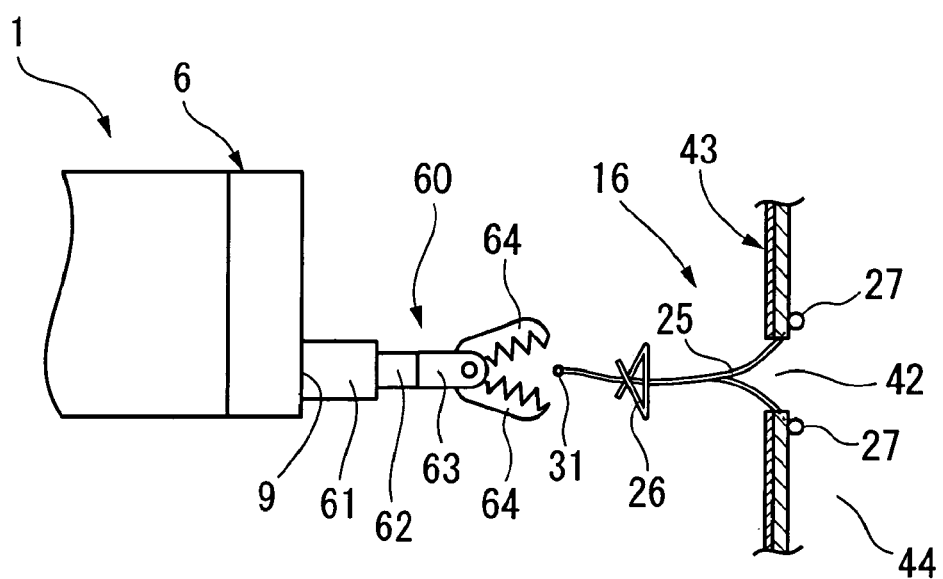
FIG. 21 is a view showing forceps for tightening the suture.
Figure 22:
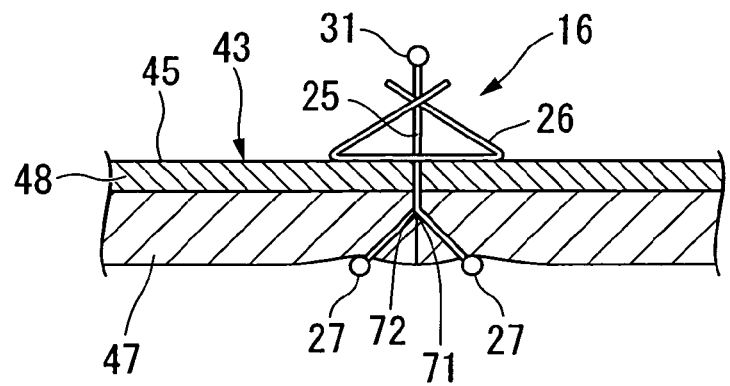
FIG. 22 is a view where the suture has been tightened, and the insertion points are made to approximately coincide.

The suture 16 is tightened as shown in FIG. 21. With the clasps 64 of the forceps 60 clasping the knot 31, the stopper 26 is pushed against the tissue by the outer sheath 61. The suture thread 25 is relatively pulled by the movement of the stopper 26. Consequently, the inner circumferential surfaces of the perforation 42 are drawn together and sealed. The suture thread 25 is pulled until the mated insertion points 71 and 72 coincide. As shown in FIG. 22, the mated muscular layers 47 and mated mucous membranes 48 exposed on the inner periphery of the perforation 42 are sealed, and the perforation 42 is closed.

In the present embodiment, the needle is diagonally inserted through the muscular layer 47 exposed on the inner periphery of the perforation 42, and the tissue is tightened by the suture thread 25 so that the insertion points 71 and 72 coincide after the anchors 27 have been stationed on the abdominal cavity 44 side, with the result that it is possible to reliably seal the mated muscular layers 47. Accordingly, the muscular layer 47 reliably knits together, and the perforation 42 can be rapidly closed. Holes are not formed in the mucous membrane from piercing by the suture thread 25.

(Third Embodiment)

A third embodiment of this invention is described with reference to drawings. Description of components and operations identical to those of the first embodiment is omitted.

Figure 23:
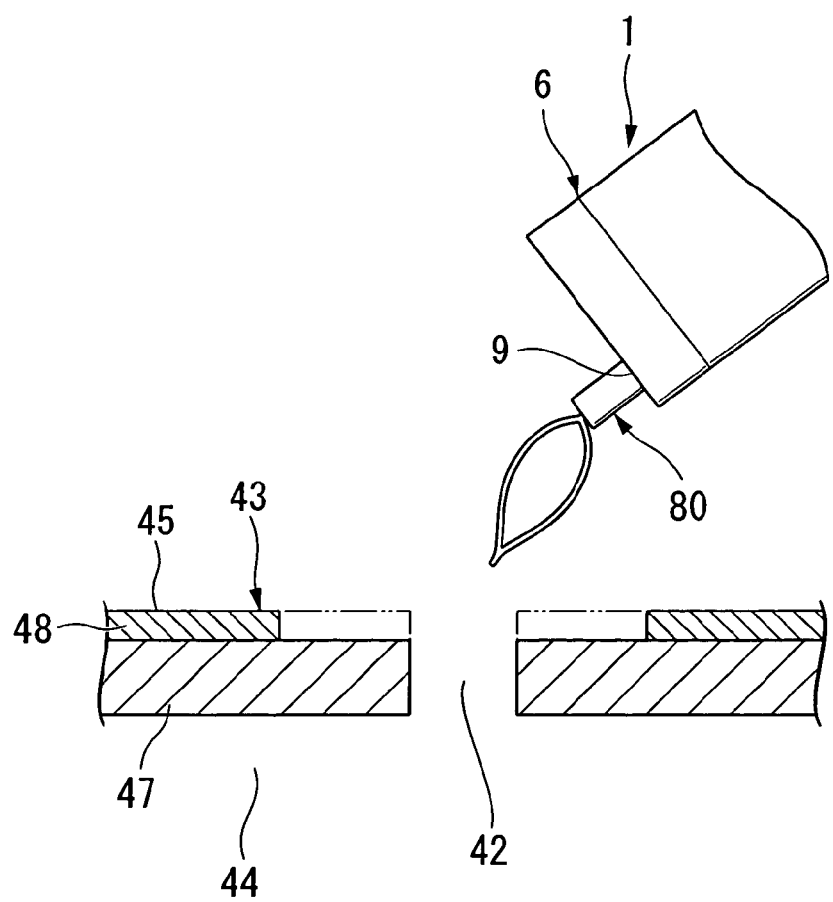
FIG. 23 is a view where the mucous membrane on the abdomen interior side is resected in the vicinity of the perforation.
Figure 24:
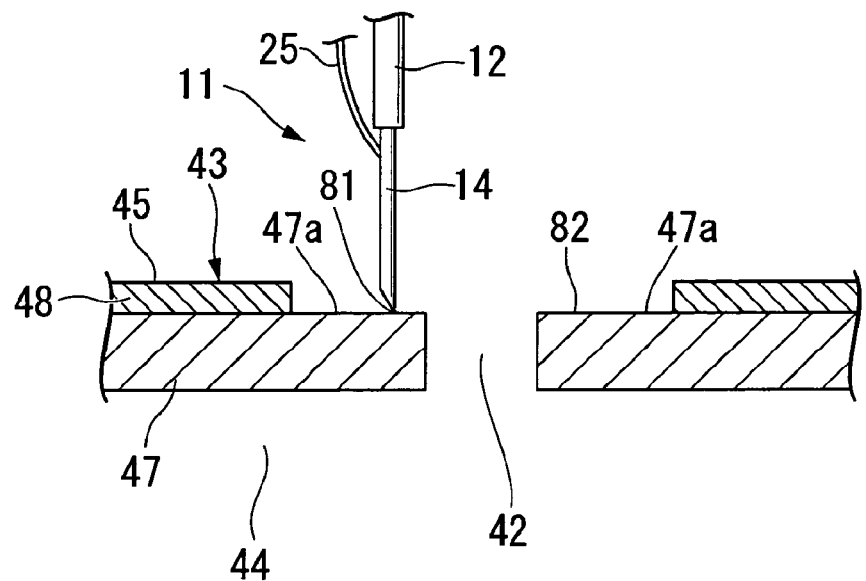
FIG. 24 is a view showing the step of inserting the needle into the surface exposed by the resection of the mucous membrane.
Figure 25:
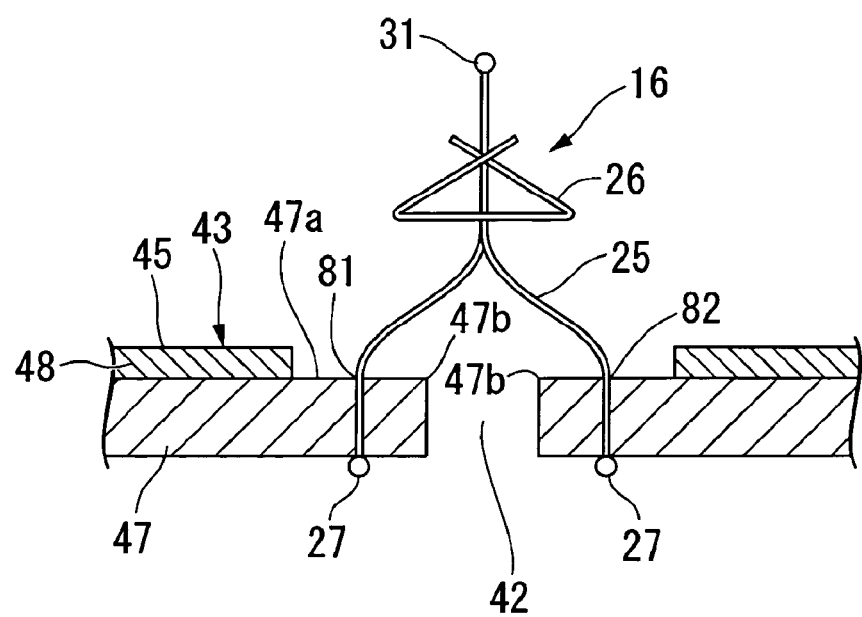
FIG. 25 is a view of the attachment of the suture.

As shown in FIG. 23, a surgical instrument 80 such as, for example, a snare is passed through the channel 9 of the endoscope insertion section 6, and the mucous membrane 48 in the vicinity of the perforation 42 is resected. When the mucous membrane 48 is resected, a suture 16 is attached by the suturing apparatus 11. As shown in FIG. 24, the needle 14 is inserted at the prescribed position (insertion point 81) of the inner surface 47a of the muscular layer 47 exposed by resection of the mucous membrane 48. When the needle 14 has pierced the muscular layer 47, and has projected into the abdominal cavity 44, the anchor 27 is pushed out. When the needle 14 is withdrawn from the muscular layer 47, the suture thread 25 runs through the muscular layer 47, and the anchor 27 is stationed on the abdominal cavity 44 side. In a similar manner, the needle 14 is again inserted at an approximately symmetrical position that sandwiches the perforation 42. The insertion point 82 in this instance is set at a place where the inner surface 47a of the muscular layer 47 is exposed by the resection of the mucous membrane 48. The muscular layer 47 is pierced by the needle 14 from the inner surface side (the interior side of the abdomen 43) to the outer surface side (the exterior side of the abdomen 43), and the second anchor 27 is pushed out. As shown in FIG. 25, when the needle 14 is pulled out, the suture 16 is attached so that it straddles the perforation 42.

Figure 26:
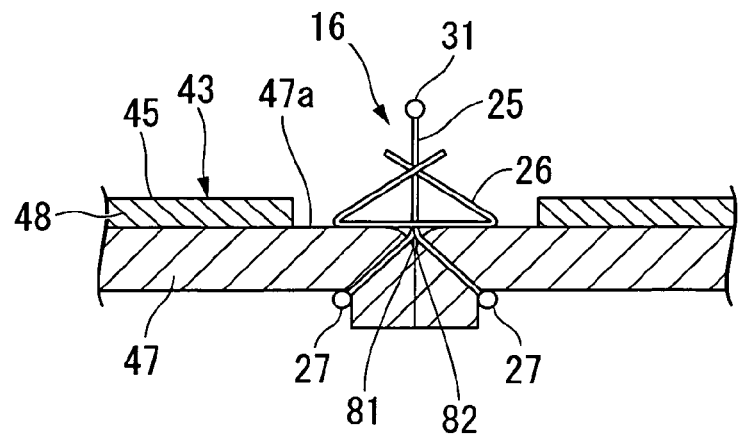
FIG. 26 is a view where the suture has been tightened, and the insertion points are made to approximately coincide.

This suture 16 is tightened as in the second embodiment. The inner circumferential surfaces of the perforation 42 are drawn together and sealed by pulling the suture thread 25. The suture thread 25 is pulled until the insertion points 81 and 82 approximately coincide. At this time, the mated end points 47b of the muscular layer 47 initially make contact on the inner side of the abdomen 43. With the point of origin set here, the mated inner surfaces 47a are drawn together. As shown in FIG. 26, the tissue is pushed outward so that the inner circumferential surfaces of the perforation 42 are oriented toward the exterior side of the abdomen 43, and the mated inner surfaces 47a of the muscular layer 47 exposed by resection of the mucous membrane 48 are sealed.

In this embodiment, the inner surfaces 47a of the muscular layer 47 at the periphery of the perforation 42 are exposed, the insertion points 81 and 82 are formed on these inner surfaces 47a, and the tissue is tightened by the suture 16 so that the insertion points 81 and 82 approximately coincide, with the result that it is possible to reliably seal the mated inner surfaces 47a of the muscular layer 47. Accordingly, the muscular layer 47 rapidly knits, and the perforation 42 can be reliably closed.

The present invention is not limited to the respective foregoing embodiments, and may be widely applied.

For example, the endoscope 1 may be inserted from the anus into the colon which is one example of a hollow organ. In this case, perforations in the colon or the like are sutured.

In the first and second embodiments, the needle 14 is almost vertically inserted relative to the muscular layer 47, but it may also be inserted with a prescribed angle of inclination. The suture thread 25 then pierces the muscular layer 47 diagonally relative to the axis of the perforation 42. In this case, as well, the same effects are obtained.

Figure 27:
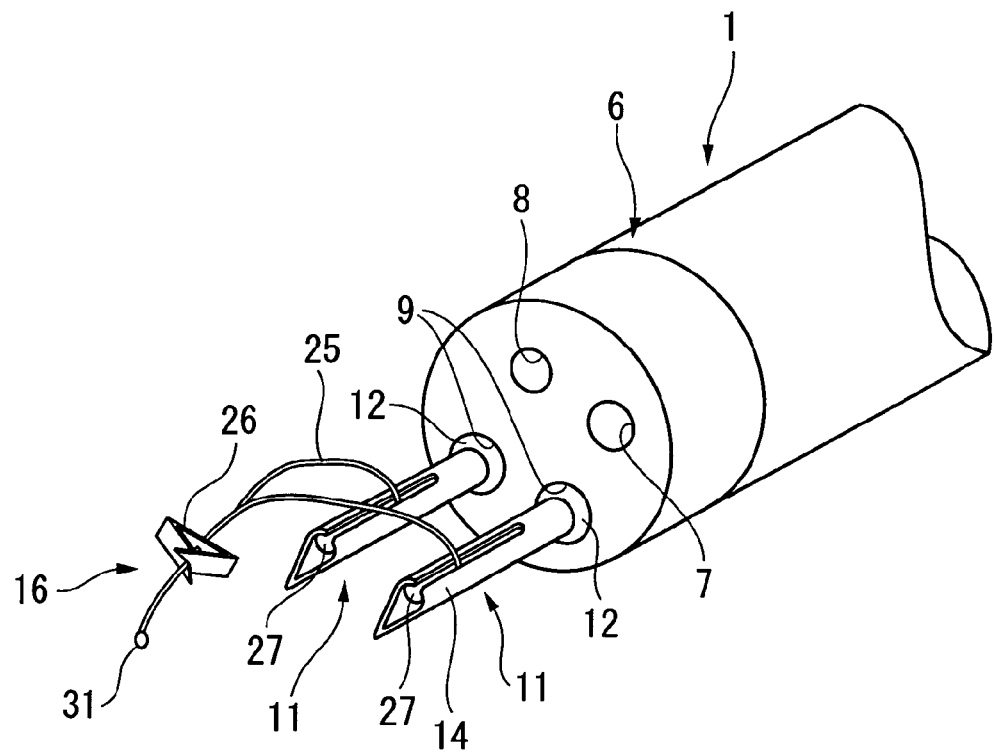
FIG. 27 is a schematic view showing one example of the combination of an endoscope and a suturing apparatus.

As shown in FIG. 27, in the case where the endoscope insertion section 6 is provided with two channels 9, it is also acceptable to run one suturing apparatus 11 each through the respective channels 9. In this case, one each of the anchors 27 of the suture 16 is housed in the respective needles 14 of each suturing apparatus 11.

What is claimed is:

1. A method for suturing a perforation formed in a wall of a luminal organ, the method comprising:
   a step of inserting an endoscope into a lumen of the luminal organ via a natural orifice, and introducing the endoscope from the lumen into an abdominal cavity via the perforation;
   a step of bending a tip of the endoscope toward the wall of the lumen organ in a state in which the endoscope is introduced via the perforation from the lumen into the abdominal cavity;
   a step of protruding a needle, inside which a first anchor and a first suture thread attached to the first anchor are housed, from a channel of the endoscope toward the wall of the luminal organ, inserting the needle through the wall from the abdominal cavity toward the lumen at a first insertion point positioned in the vicinity of the perforation, and delivering the first anchor into the lumen to attach the first suture thread to the luminal organ;
   a step of withdrawing the needle from the wall of the luminal organ after delivering the first anchor into the lumen to attach the first suture thread to the luminal organ such that a portion of the first suture thread extends into the abdominal cavity;
   a step of protruding the needle, inside which a second anchor and a second suture thread attached to the second anchor are housed, from the channel of the endoscope toward the wall of the luminal organ, inserting the needle through the wall from the abdominal cavity toward the lumen at a second insertion point positioned in the vicinity of the perforation and opposite to the first insertion point with the perforation positioned between the first insertion point and the second insertion point, and delivering the second anchor into the lumen to attach the second suture thread to the luminal organ;
   a step of withdrawing the needle from the wall of the luminal organ after delivering the second anchor into the lumen to attach the second suture thread to the luminal organ such that a portion of the second suture thread extends into the abdominal cavity; and
   a step of sealing
      a muscular layer of the wall of the luminal organ, which is located between the first insertion point and the perforation and faces the abdominal cavity, with
      a muscular layer of the wall of the luminal organ, which is located between the second insertion point and the perforation and faces the abdominal cavity,
   by pulling the portion of the first suture thread extending into the abdominal cavity and the portion of the second suture thread extending into the abdominal cavity into the lumen of the luminal organ through the perforation.

2. The method according to claim 1, wherein the needle is inserted into the lumen of the luminal organ via a tool that is inserted via the channel of the endoscope from the natural orifice in a living body.

3. The method according to claim 1, wherein in the steps of inserting the needle through the wall from the abdominal cavity toward the lumen to deliver the first anchor and the second anchor, the needle is pierced into an innermost surface of the wall of the luminal organ facing the lumen.

4. The method according to claim 1, wherein in the step of sealing,
   the muscular layer of the wall of the luminal organ, which is located between the first insertion point and the perforation and faces the abdominal cavity, and
   the muscular layer of the wall of the luminal organ, which is located between the second insertion point and the perforation and faces the abdominal cavity,
are bent toward the lumen to be substantially parallel to each other and to contact each other.

* * * * *